United States Patent [19]

Starzewski et al.

[11] Patent Number: 4,620,021

[45] Date of Patent: Oct. 28, 1986

[54] ORGANIC NICKEL COMPOUNDS, PRODUCTION AND USE THEREOF AS CATALYSTS IN THE POLYMERIZATION OF OLEFINS

[75] Inventors: Karl-Heinz A. O. Starzewski, Bad Vilbel; Josef Witte, Cologne; Herbert Bartl, Odenthal, all of Fed. Rep. of Germany

[73] Assignee: Bayer Aktiengesellschaft, Leverkusen, Fed. Rep. of Germany

[21] Appl. No.: 654,227

[22] Filed: Sep. 25, 1984

[30] Foreign Application Priority Data

Oct. 7, 1983 [DE] Fed. Rep. of Germany ....... 3336500

[51] Int. Cl.[4] ............................................. C07F 15/04
[52] U.S. Cl. ........................................ 556/19; 556/21; 556/22; 585/502; 585/513
[58] Field of Search ............... 260/439 R; 556/19, 21, 556/22

[56] References Cited

U.S. PATENT DOCUMENTS 4,097,509  6/1978  Schmidbaur et al. ...... 260/429 R X
4,185,028  1/1980  Schmidbaur et al. .............. 260/430
4,293,502  10/1981  Beach et al. .................... 260/439 R
4,529,554  7/1985  Beach et al. ........................ 556/22
4,537,982  8/1985  Starzewski et al. ................. 556/14

OTHER PUBLICATIONS

Empsall et al, J. Chem. Soc., Dalton Trans., (15) 1500–1506 (1976).

Primary Examiner—Helen M. S. Sneed
Attorney, Agent, or Firm—Connolly and Hutz

[57] ABSTRACT

Olefins such as ethylene can be polymerized with a catalyst which comprises nickel compounds obtained by reacting a nickel-(O) compound or a nickel compound which may be converted in situ into a nickel-(O) compound with an adduct or a mixture of a quinoid compound and a tertiary phosphine and with a compound corresponding to the following general formula:

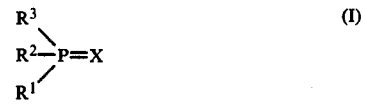

wherein
$R^1$, $R^2$ and $R^3$ independently represent $C_1$–$C_{20}$ alkyl, $C_2$–$C_{20}$ alkenyl, $C_6$–$C_{12}$ aryl or $C_3$–$C_8$ cycloalkyl optionally substituted by halogen, hydroxy, $C_1$–$C_{20}$ alkoxy, nitro or $C_6$–$C_{12}$ aryloxy; also $C_6$–$C_{12}$ aryl-$C_1$–$C_{20}$ alkyl, $C_6$–$C_{12}$ aryl-$C_2$–$C_{20}$ alkenyl, $C_1$–$C_{20}$ alkyl-$C_6$–$C_{12}$ aryl, $C_1$–$C_{20}$ alkyl-$C_3$–$C_8$ cycloalkyl and $C_6$–$C_{12}$ aryl-$C_3$–$C_8$ cycloalkyl, di-$C_1$–$C_4$ alkylamino, optionally substituted phenoxy or alkoxy; $R^4$, $R^5$ and $R^6$ represent hydrogen, silyl, halogen, cyano or $R^1$ and X represents O, $NR_4$ or

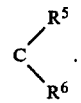

6 Claims, No Drawings

ORGANIC NICKEL COMPOUNDS, PRODUCTION AND USE THEREOF AS CATALYSTS IN THE POLYMERIZATION OF OLEFINS

This invention relates to nickel compounds obtained by reacting a nickel-(O) compound or a nickel compound which may be converted in situ into a nickel-(O) compound with an adduct or a mixture of a quinoid compound and a tertiary phosphine and with a compound corresponding to the following general formula:

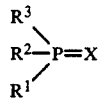
(I)

and to the use thereof as catalysts in the polymerization of olefins.

DE-OS No. 29 23 206 describes a process for the production of polyethylene waxes which is characterised in that ethylene is polymerized in a solvent mixture of an aromatic hydrocarbon and a hydroxyl group-containing solvent at a temperature of from 50° to 100° C. and under an excess pressure of from 0.7 to 350 bars using a catalyst consisting of (a) a O-valent nickel compound and (b) an adduct and/or mixture of a quinoid compound and a tertiary phosphine.

The polyethylene obtained has a low molecular weight, the activity of the catalyst is weak and the process very restricted in the choice of solvents.

It has now surprisingly been found that these disadvantages may be overcome and that polyolefin waxes and also polyolefin plastics of medium, high and ultra-high molecular weight may be specifically obtained using certain new nickel catalysts.

Accordingly, the present invention relates to nickel compounds obtained by reacting a nickel-(O) compound or a nickel compound which may be converted in situ into a nickel-(O) compound with an adduct or a mixture of a quinoid compound and a tertiary phosphine and with a compound corresponding to the following general formula:

(I)

wherein $R^1$, $R^2$ and $R^3$ independently represent $C_1$-$C_{20}$ alkyl, $C_2$-$C_{20}$ alkenyl, $C_6$-$C_{12}$ aryl or $C_3$-$C_8$ cycloalkyl optionally substituted by halogen, hydroxy, $C_1$-$C_{20}$ alkoxy, nitro or $C_6$-$C_{12}$-aryloxy; also $C_6$-$C_{12}$ aryl-$C_1$-$C_{10}$ alkyl $C_1$-$C_{20}$ alkyl-$C_6$-$C_{12}$ aryl, $C_6$-$C_{12}$ aryl-$C_2$-$C_{20}$ alkenyl, $C_1$-$C_{20}$ alkyl-$C_3$-$C_8$ cycloalkyl and $C_6$-$C_{12}$ aryl-$C_3$-$C_8$ cycloalkyl, di-$C_1$-$C_4$ alkylamino, optionally substituted phenoxy or alkoxy;

$R^4$, $R^5$ and $R^6$ represent hydrogen, silyl, halogen, cyano or $R^1$; and

X represents O, $NR^4$ or

Suitable tertiary phosphines correspond to the following general formula:

(II)

wherein $R^7$, $R^8$ and $R^9$ independently represent $C_1$-$C_{20}$ alkyl, $C_6$-$C_{12}$ aryl, $C_2$-$C_{30}$ alkenyl or $C_3$-$C_8$ cycloalkyl optionally substituted by halogen, hydroxy, $C_1$-$C_{20}$ alkoxy or $C_6$-$C_{12}$ aryloxy; also $C_6$-$C_{12}$ aryl-$C_1$-$C_{20}$ alkyl, $C_1$-$C_{20}$ alkyl-$C_6$-$C_{12}$ aryl, halogen, hydroxy, $C_1$-$C_{20}$ alkoxy or $C_6$-$C_{12}$ aryloxy.

Suitable quinoid compounds are o- or p-quinoid compounds of the benzenes and naphthalene series and also anthraquinones which may also be substituted.

Examples of such quinoid compounds are p-benzoquinone, chloranil, 1,4-naphthoquinone and 9,10-anthraquinone.

Preferred radicals $R^1$, $R^2$ and $R^3$ are $C_1$-$C_6$ alkyl, cyclohexyl, phenyl, tolyl, benzyl, di-$C_1$-$C_4$ alkylamino, phenoxy and methoxy.

Preferred radicals $R^4$, $R^5$ and $R^6$ are hydrogen, $C_1$-$C_6$ alkyl, phenyl, $C_1$-$C_4$ alkyl-phenyl, chlorophenyl, nitrophenyl, trimethylsilyl, chlorine and cyano.

$R^7$, $R^8$ and $R^9$ are preferably cyclohexyl, phenyl, tolyl, benzyl, vinyl and $C_1$-$C_4$ alkyl.

Ni(cyclooctadiene)$_2$ and Ni(allyl)$_2$ are mentioned as examples of nickel-(O) compounds.

Examples of nickel compounds which may be converted in situ into nickel-(O) compounds are Ni-acetylacetonate, Ni-octanoate and Ni-stearate which may be reduced using conventional reducing agents, such as boranate, alanate, aluminium alkyls or lithium organyls.

As far as is known at the present time, the nickel compounds according to the present invention correspond to the following general formula:

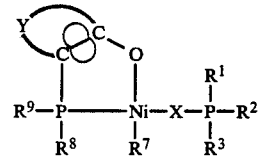
(III)

wherein $R^1$, $R^2$, $R^3$, $R^7$, $R^8$, $R^9$ and X are as defined above; and Y represents the remaining member of a hydroxy-substituted aromatic system.

From 1 to 4 moles of the quinoid compound and of the tertiary phosphine and from 1 to 4 moles of the compound (I) are preferably used per mole of nickel-(O) compound. It is particularly preferred to use 1 mole of quinoid compound and the tertiary phosphine and 1 mole of the compound (I) per mole of the nickel-(O) compound.

The reaction temperature is from 0° to 100° C., more perferably from 20° to 70° C.

The reaction is carried out in the absence of oxygen, preferably in a solvent which must be inert to the reactants, such as benzene, toluene, cyclohexane and n-hexane.

On completion of the reaction, the catalyst is generally used direction, i.e. without isolation, for the polymerization of olefins. The reaction mixture may also be filtered, in which case, the filtrate containing the catalyst may be used for polymerization. The catalyst may also be isolated by concentrating the reaction mixture or by concentrating and/or cooling the filtrate.

It is also possible to produce the catalyst in the presence of the olefins to be polymerized.

The present compounds are readily transportable and meterable, are catalytically active in a number of solvents and are active over a wide temperature range and over a wide pressure range.

The present invention also relates to the use of the present nickel compounds as catalysts in the polymerization of olefins, particularly ethylene.

The quantity of nickel compound used is not critical. Typical catalyst concentration amount to from $10^{-2}$ to $10^{-4}$ moles per liter. The quantity of catalyst used, based on ethylene, amounts to from 0.005 to 10%, by weight, preferably from 0.01 to 0.1%, by weight.

The following procedures are suitable for the polymerization of olefins using the catalysts according to the present invention:

(a) initially introducing the solid, dissolved or suspended catalyst (or its components) and adding the olefins, followed by heating (b) initially introducing the olefin and then injecting the catalyst solution or suspension (or its components)

(c) continuously introducing the catalyst solution or suspension (or its components) under the desired polymerization conditions determined in advance (temperature, pressure) to form the olefin.

The polymerization reaction may be carried out in a solvent or diluent or suspending agent, such as aliphatic hydrocarbons, such as n-hexane and cyclohexane; aromatic hydrocarbons, such as benzene, toluene and xylene; ketones, such as acetone and methyl ethyl ketone; esters, such as ethyl acetate; acid amides, such as dimethyl formamide; and ethers, such as tetrahydrofuran. Polymerization may be carried out continuously or in batches.

The polymerization temperature is preferably from 20° to 200° C., more preferably from 60° to 130° C. The olefin pressure to be applied amounts to at least 1 bar, preferably from 5 to 1000 bars.

EXAMPLE 1

The catalyst according to the present invention consisting of 2 mMoles of bis-cyclooctadiene nickel-(O), 2 mMoles of the triphenylphosphine/p-benzoquinone adduct and 2 mMoles of component I as listed in the following Table in 50 ml of toluene is injected into the prepared autoclave which contains 1 liter of solvent. After a polymerization time of from 1 to 3 hours, the polymerization mixture is left to cool, the autoclave is vented and the solid polyethylene isolated by filtration. The filtrate is analyzed by gas chromatography. After removal of the solvent in a rotary evaporator, the quantity of oligomers may be weighed out. Accordingly, the low-boiling fractions are not included in the yields quoted (sum of polymers and oligomers) or in the calculated activities (moles of ethylene reacted per mole of nickel).

The reaction conditions and results are shown in the following Table, in which

A = component (I)
B = type of solvent
C = ethylene pressure [bars]
D = temperature [°C.]
E = polyethylene yields (percentage of oligomers)
F = catalyst activity (moles of ethylene per mole of Ni)
G = polyethylene melting point [°C.]
H = intrinsic viscosity η in tetralin at 140° C. [dl/g]
I = density ρ [g/cc]

TABLE

| Example No. | A | B | C | D | E | F | G | H | I |
|---|---|---|---|---|---|---|---|---|---|
| 1 | $(C_6H_5)_3P=O$ | cyclohexane | 100 | 65–85 | 723 (0) | 12911 | 132 | 9.60 | 0.968 |
| 2 | $(C_6H_5O)_3P=O$ | " | 100 | 60–100 | 965 (0) | 17232 | 135 | 5.85 | 0.960 |
| 3 | $(CH_3)_3P=O$ | " | 100 | 75–80 | 709 (0) | 12661 | 136 | 4.29 | 0.968 |
| 4 | $[(CH_3)_2N]_3P=O$ | " | 100 | 90 | 826 (0) | 14750 | 134 | 2.43 | 0.972 |
| 5 | $(CH_3O)_3P=O$ | " | 100 | 90–100 | 830 (0) | 14821 | 130 | 1.40 | 0.969 |
| 6 | $(C_6H_5)_3P=N-C(CH_3)_3$ | " | 100 | 100 | 648 (0) | 11571 | 130 | 3.28 | 0.971 |
| 7 | $(C_6H_5)_3P=N-Si(CH_3)_3$ | " | 100 | 90 | 540 (0) | 9643 | 133 | 3.15 | 0.973 |
| 8 | $(C_6H_5)_3P=CH-CH_3$ | " | 100 | 100 | 1143 (0) | 20411 | 129 | 2.14 | 0.966 |
| 9 | $(C_6H_5)_3P=CH-C(CH_3)=CH_2$ | " | 100 | 90–100 | 735 (0) | 13125 | 129 | 1.50 | 0.964 |
| 10 | $(C_6H_5)_3P=CH-CH=CH-C_6H_5$ | " | 100 | 90–100 | 735 (0) | 13125 | 132 | 3.40 | 0.964 |
| 11 | $(C_6H_5)_3P=CH-C_6H_5$ | " | 100 | 90 | 515 (0) | 9196 | 134 | 2.90 | 0.971 |
| 12 | $(C_6H_5)_3P=C(C_6H_5)_2$ | " | 100 | 110–120 | 725 (0) | 12946 | 130 | 1.52 | 0.970 |
| 13 | $(C_6H_5)_3P=CH-CH_3$ | n-hexane | 100 | 100 | 933 (0) | 17732 | 132 | 1.80 | 0.966 |
| 14 | $(C_6H_5)_3P=CH-CH_3$ | toluene | 100 | 80–100 | 673 (0) | 12018 | 132 | 2.05 | 0.969 |
| 15 | $(C_6H_5)_3P=CH-CH_3$ | methyl acetate | 100 | 100 | 915 (0) | 16339 | 122 | 0.21 | 0.945 |
| 16 | $(C_6H_5)_3P=CH-CH_3$ | acetone | 100 | 100 | 583 (0) | 10411 | 115 | 0.16 | 0.955 |
| 17 | $(C_6H_5)_3P=CH-CH_3$ | dimethyl formamide | 100 | 100 | 105 (6) | 1875 | 122 | 0.12 | 0.964 |
| 18 | $(C_6H_5)_3P=CH-CH_3$ | t-butanol | 100 | 100 | 556 (0) | 9929 | 110 | 0.18 | — |
| 19 | $(C_6H_5)_3P=CH-CH_3$ | methanol | 100 | 80 | 445 (4) | 8125 | 79 | 0.02 | — |

We claim:

1. Nickel compounds obtained by reacting a nickel-(O) compound or a nickel compound which may be converted in situ into a nickel-(O) compound with an adduct or a mixture of a quinoid compound and a tertiary phosphine and with a compound corresponding to the following general formula:

wherein $R^1$, $R^2$ and $R^3$ independently represent $C_1$–$C_{20}$ alkyl, $C_2$–$C_{20}$ alkenyl, $C_6$–$C_{12}$ aryl or $C_3$–$C_8$ cycloalkyl optionally substituted by halogen, hydroxy, $C_1$–$C_{20}$ alkoxy, nitro or $C_6$–$C_{12}$ aryloxy; also $C_6$–$C_{12}$ aryl-$C_1$–$C_{20}$ alkyl, $C_6$–$C_{12}$ aryl-$C_2$–$C_{20}$ alkenyl, $C_1$–$C_{20}$ alkyl-$C_6$–$C_{12}$ aryl, $C_1$–$C_{20}$ alkyl-$C_3$–$C_8$ cycloalkyl and $C_6$–$C_{12}$ aryl-$C_3$–$C_8$ cycloalkyl, di-$C_1$–$C_4$ alkylamino, optionally substituted phenoxy or alkoxy; $R^4$, $R^5$ and $R^6$ represent hydrogen, silyl, halogen, cyano or $R^1$ and X represents O, $NR^4$ or

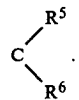

2. Compounds as claimed in claim 1 wherein $R^1$, $R^2$ and $R^3$ represent $C_1$–$C_6$ alkyl, cyclohexyl, phenyl, tolyl, benzyl, di-$C_1$–$C_4$ alkylamino, phenoxy or methoxy; $R^4$, $R^5$ and $R^6$ represent hydrogen, $C_1$–$C_6$ alkyl, phenyl, $C_1$–$C_4$ alkyl-phenyl, chlorophenyl, nitrophenyl, trimethylsilyl, chlorine or cyano;

the tertiary phosphine corresponds to the following general formula:

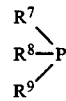

wherein $R^7$, $R^8$ and $R^9$ represent cyclohexyl, phenyl, tolyl, benzyl, vinyl or $C_1$–$C_4$-alkyl;

and an optionally substituted o- or p-quinoid compound of the benzene or naphthalene series or anthraquinone is used as the quinoid compound.

3. A process for producing the nickel compounds claimed in claim 1 wherein a nickel-(O) compound or a compound which may be converted in situ into a nickel-(O) compound is reacted with an adduct or a mixture of a quinoid compound and a tertiary phosphine and with a compound corresponding to the following general formula:

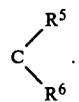

wherein $R^1$, $R^2$, $R^3$ and X are as defined in claim 1; in the absence of oxygen.

4. A process as claimed in claim 3, wherein from 1 to 4 moles of the quinoid compound, the tertiary phosphine and the compound (I) are used per mole of nickel-(O) compound.

5. A process as claimed in claim 3, wherein the reaction is carried out at from 0° to 100° C. in an inert solvent.

6. A process for producing the nickel compounds claimed in claim 2 wherein a nickel-(O) compound or a compound which may be converted in situ into a nickel-(O) compound is reacted with an adduct or a mixture of a quinoid compound and a tertiary phosphine and with a compound corresponding to the following general formula:

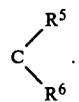

wherein $R^1$, $R^2$, $R^3$ and X are as defined in claim 2; in the absence of oxygen.

* * * * *